US00PP26414P3

(12) United States Plant Patent
Johansson

(10) Patent No.: US PP26,414 P3
(45) Date of Patent: Feb. 16, 2016

(54) **MAPLE TREE (*ACER TRUNCATUM*)NAMED 'SUPER DRAGON'**

(50) Latin Name: *Acer truncatum*
Varietal Denomination: Super Dragon

(71) Applicant: Keith G. Johansson, Arlington, TX (US)

(72) Inventor: Keith G. Johansson, Arlington, TX (US)

( * ) Notice: Subject to any disclaimer, the term of this patent is extended or adjusted under 35 U.S.C. 154(b) by 34 days.

(21) Appl. No.: 13/815,603

(22) Filed: May 22, 2013

(65) Prior Publication Data

US 2014/0352012 P1 Nov. 27, 2014

(51) Int. Cl.
*A01H 5/00* (2006.01)

(52) U.S. Cl.
USPC ..... Plt./224

(58) Field of Classification Search
USPC ..... Plt./224
See application file for complete search history.

(56) References Cited

U.S. PATENT DOCUMENTS

| | | | |
|---|---|---|---|
| PP4,654 | P | 2/1981 | Siebenthaler |
| PP11,295 | P | 3/2000 | Moon |
| PP11,322 | P | 4/2000 | Hanson |
| PP17,367 | P3 | 1/2007 | Johansson |

*Primary Examiner* — Susan McCormick Ewoldt
(74) *Attorney, Agent, or Firm* — Guy V. Manning

(57) ABSTRACT

A novel variety of the maple tree *Acer truncatum* was discovered in North Texas. It has a smaller mature size than typical Shantung maple mature size, and its leaves have an unusually deep cut between lobes, extending about two-thirds (⅔) of the distance from tip to base, with a distinctively elongate and narrow (almost thread-like) unfurling central lobe that widens as it matures. It exhibits consistent yellow-green leaf color throughout the spring, summer and fall, developing striking red-orange and yellow-pink coloration variations in the fall. Its coloration contrasts sharply to its lighter yellow-green veins which appear almost white and enhanced as the leaf darkens somewhat during summer. The variety known as 'Super Dragon' also is extremely tolerant to direct summer sun and drought conditions.

12 Drawing Sheets

Latin name of the genus and species: *Acer truncatum.*

And the variety denomination of the plant claimed: 'Super Dragon'.

BACKGROUND OF THE INVENTION

1. Field of the Invention

This invention relates generally to a new and distinct variety of decorative maple tree known generally by the scientific name *Acer truncatum.* I discovered it growing in a cultivated area in my nursery in Fort Worth, Tex., in 2006. I have given it the name 'Super Dragon' because of its noticeable and distinctive yellow-green leaves and orange and pink-to-red new growth colors.

No federally sponsored research or development was involved in this invention.

2. Background

Maple trees provide desirable shade from spring to fall and typically shed their leaves for winter, thereby providing useful surrounding vegetation where summer sunlight may be excessive and winter sunshine is desirable. Displaying striking colors, maple trees are characteristically ornamental and provide pleasing and varying visual effects throughout their foliage period.

The *Acer truncatum* maple tree, commonly called "Shantung" maple, is a newly introduced tree in the United States which does exceptionally well in the Midwest in hot climates and heavily alkaline soils. Typical fifteen year old Shantaung maple trees stand upright and are twenty-eight to thirty-four feet tall, with a spread of twenty to twenty-six feet. Shantung maple leaves generally are characterized by having truncated base lobes near the leaf petiole and by having a prominent central lobe, giving the leaf a distinctly ovate-truncate shape. Fall foliage appears yellow, with occasional areas of lesser reds or orange mixed with yellow, though the latter seldom is repeated in subsequent years.

The instant novel variety of maple tree now discovered exhibits striking yellow-green colors throughout its growing season, along with red, orange and yellow spring colors and pink to orange and red summer growth. Other *Acer truncatum* species are prone to exhibit green or reddish-purple new growth in warm weather, but the instant novel variety has never done so.

The instant novel variety of maple tree also thrives in full sun, even Texas summer sun, whereas other yellow-leaf maples cultivars easily burn in direct summer sunlight during heat waves, even in northern climates.

SUMMARY OF THE INVENTION

The novel cultivar of the present invention, named *Acer truncatum* 'Super Dragon', is believed to be a variant of an unknown *Acer truncatum* but distinguished by good heat tolerance, including tolerance to direct sun, and a consistent yellow-green leaf color throughout the spring, summer and fall, developing striking red-orange and yellow-pink coloration variations in the fall, and a smaller mature size. Specifically:

(a) its leaves have an unusually deep cut between lobes, extending about two-thirds (⅔) of the distance from tip to base, with a distinctively elongate and narrow (almost thread-like) unfurling central lobe that widens as it matures;

(b) its yellow-green leaf colors contrast sharply to the lighter yellow-green veins, appearing almost white and enhanced as the leaf darkens somewhat during summer;
(c) it is smaller than typical Shantung maple mature size; and
(d) it is tolerant to direct summer sun and drought conditions, unusual for a maple leaf with its color.

DETAILED DESCRIPTION OF THE INVENTION

The instant variety of maple tree was discovered as a seedling growing among a group of other maple tree seedlings of the *Acer truncatum* species at my nursery in Fort Worth, Tex., in 2006. It was successfully asexually reproduced at said nursery by grafting onto other *Acer truncatum* seedlings and by semi-hardwood cuttings. The novel characteristics are reliably transmitted to succeeding generations.

With reference to the six (6 y.o.) year old trees depicted in the figures, the following specific description of the instant maple variety details its unique characteristics. Color terminology refers to The 2001 Royal Horticultural Society (R.H.S.) Colour Chart.

Origin: A tree of unknown origin, 'Super Dragon' maples are similar to other *Acer truncatum* varieties except for spring, summer and fall leaf coloration, leaf shape, a notable tolerance for exposure to direct sun and heat conditions.

Classification: *Acer truncatum* 'Super Dragon'.

Parentage: Unknown; believed to be a seedling variation, mutation or adaptation of *Acer truncatum.*

Figure 1A:
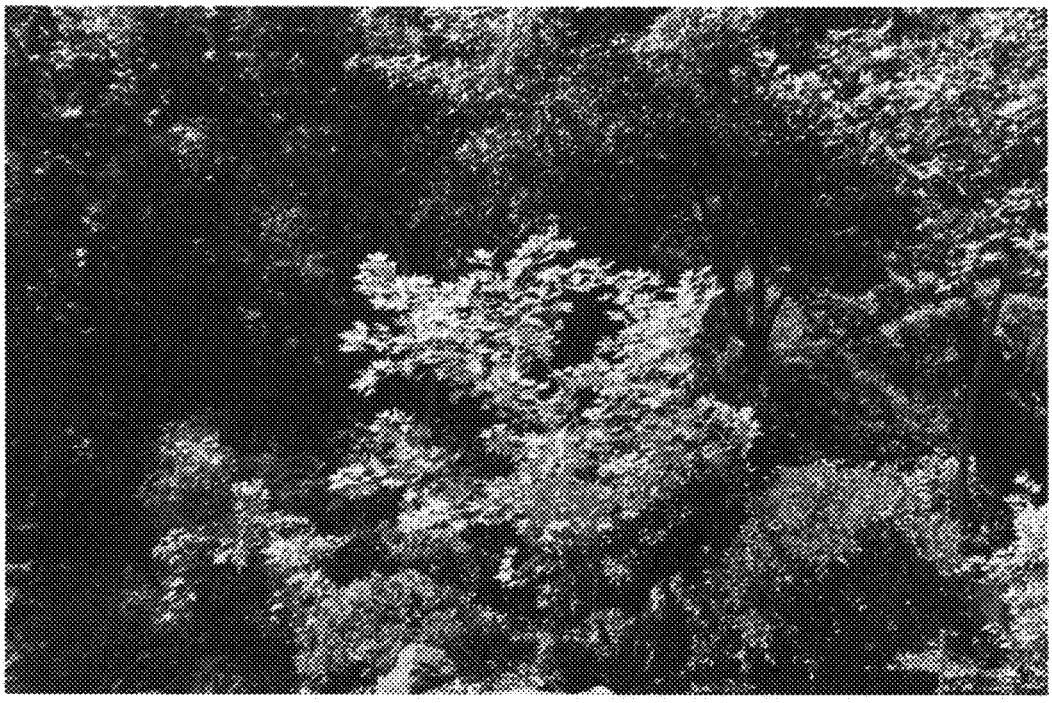
FIGS. 1A-1C are photographic views of several examples of the mature original tree of the present invention in differing settings, from crowded undergrowth (FIG. 1A), roadside (FIG. 1B) and open field (FIG. 1C), all in summer.
Figure 1B:
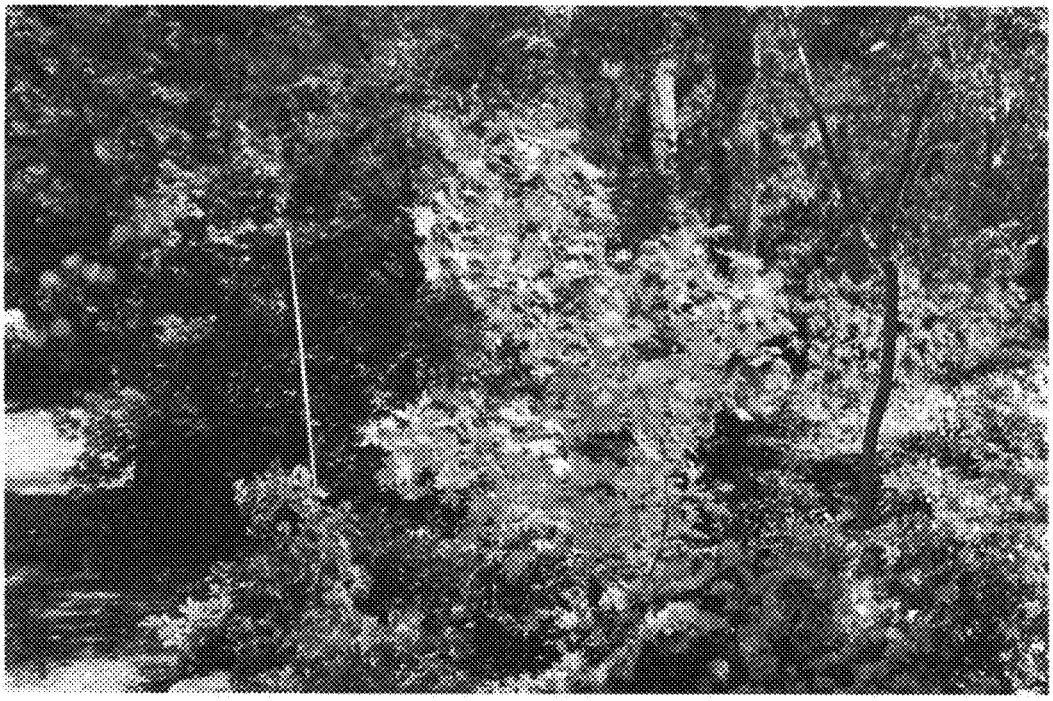
Figure 1C:
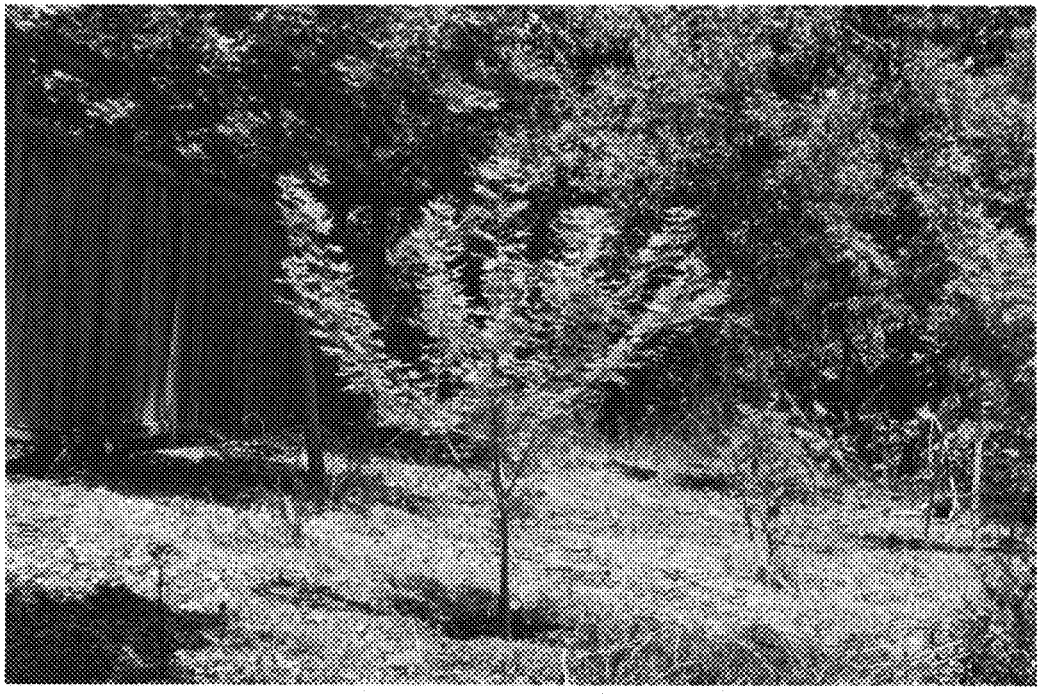
Figure 1D:
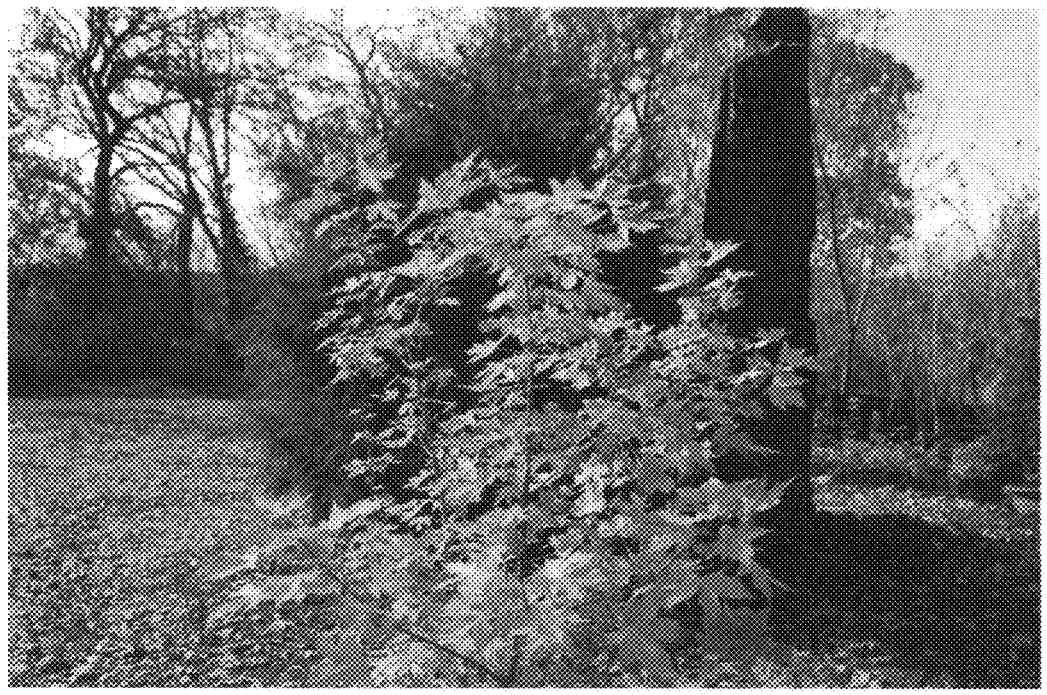
FIGS. 1D-1E are photographic views of the upper portions of the examples of the mature original tree of the present invention in fall.
Figure 1E:
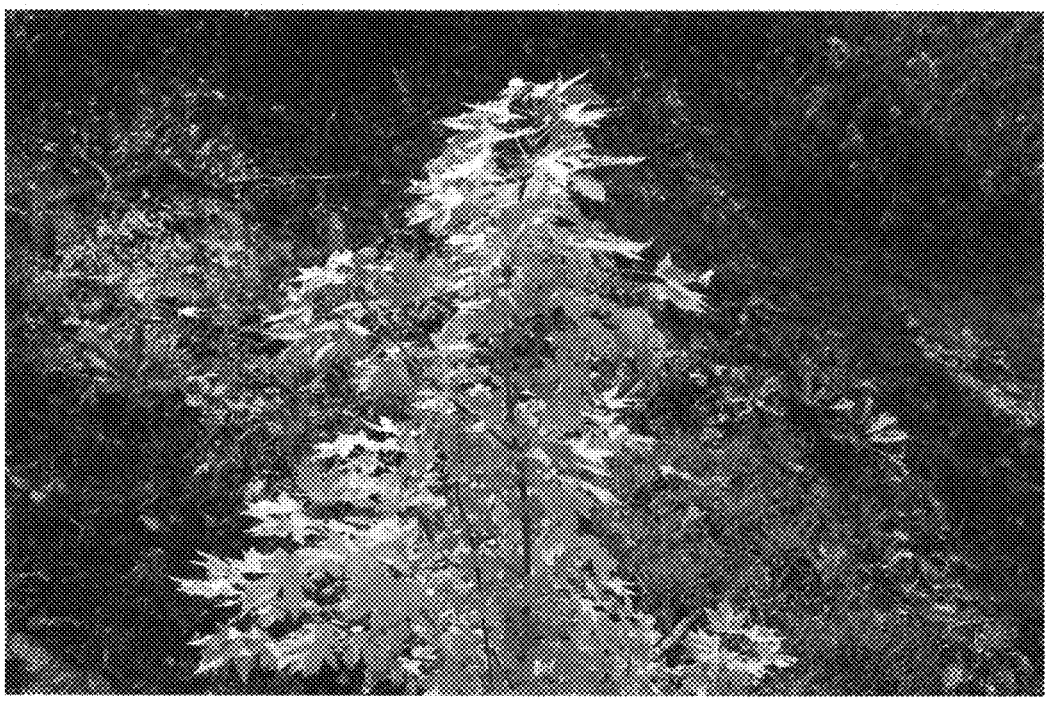
Figure 2A:
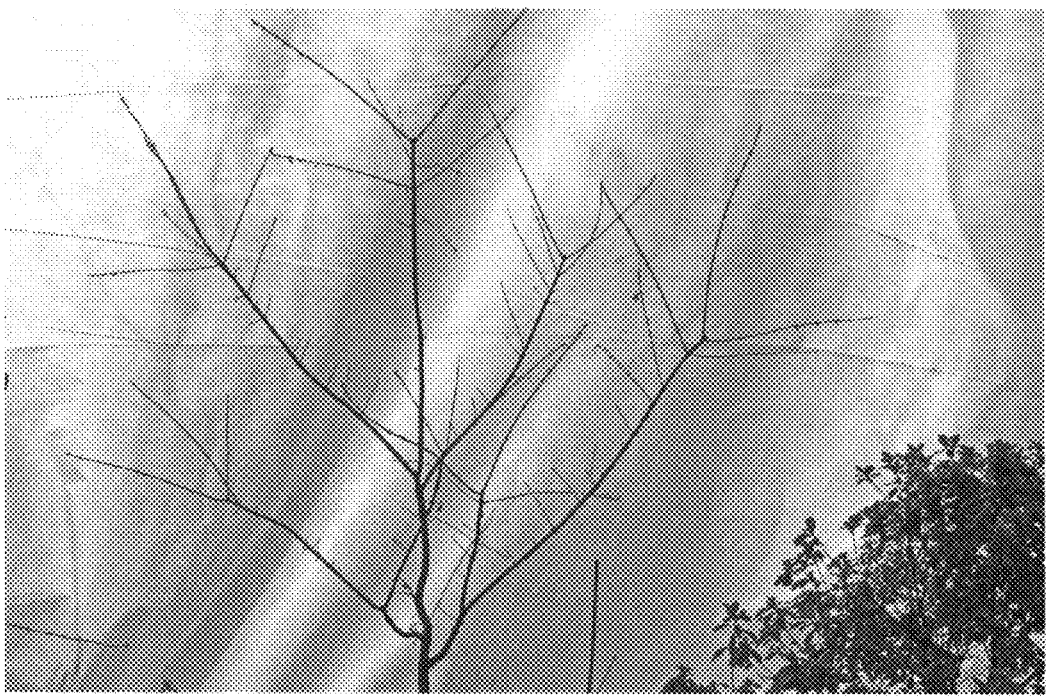
FIG. 2A is a photographic view of the mature original tree of FIG. 1A in winter, showing bare limbs and typical branch structure.
Figure 2C:
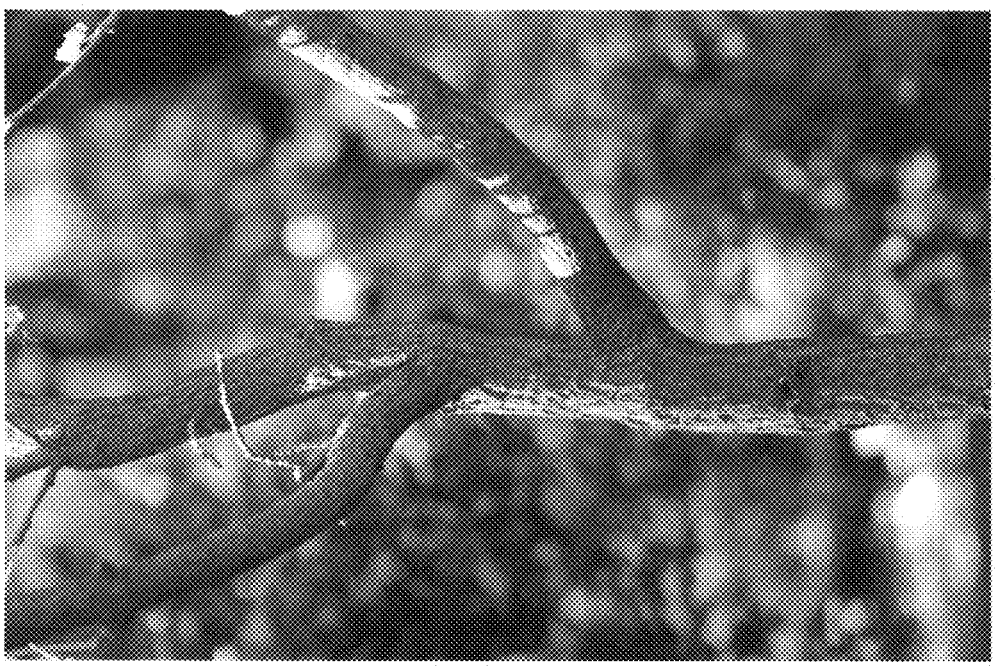
FIG. 2C is a photographic close-up view of the major branches of the mature original tree of FIG. 1A.
Figure 2B:
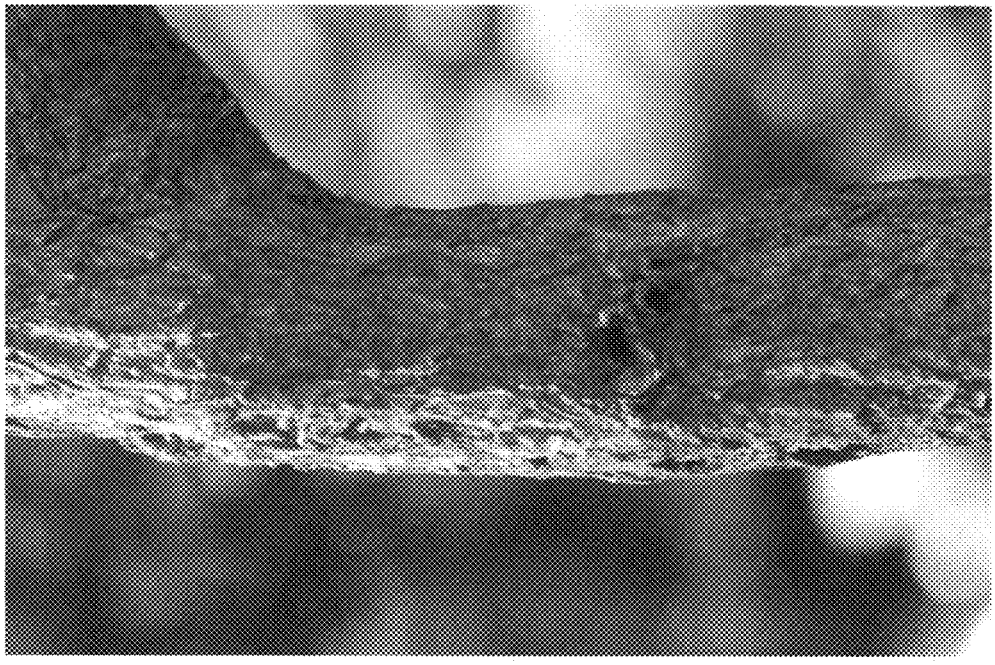
FIG. 2B is a photographic close-up view of the mature original tree of FIG. 1A showing the tree's bark characteristics.

Shape: Deciduous tree with rounded, open crown of uniform spread and many vigorous, crowded branches. See FIGS. 1A-2B. Caliper size is one (1") inch in six (6) years, measured eighteen (18") inches up from ground level. A low-branched trunk produces a shrubby tree if left alone (FIG. 1A), but if pruned to four (4) or more feet before being allowed to branch, if produces a more upright shade tree (FIGS. 1B-1C).

Height: Two (2 m) meters at six (6) years, increasing less than one-half (0.5 m/yr) meter per year, slowing with age but expected to reach five to seven (5-7 m) meters at maturity, smaller than typical of *Acer truncatum* (12-15 meters at maturity). See FIGS. 1A-1C. Grafted trees grow faster, typically one-half (0.5 m/yr) meter per year, but other growth factors are the same on grafted and own-root trees.

Spread: Comparatively slow growth results in a rounded crown of equal spread. Two (2 m) meters at six (6) years, increasing an average of one-half (0.5 m/yr) meter per year, slowing with age but expected to reach five to seven (5-7 m) meters at maturity, smaller than typical of *Acer truncatum* (12-15 meters at maturity). The instant maple variety, 'Super Dragon', can be a typically low-branched, shrubby tree, but it lends itself to pruning into a straight trunk of four (4 ft.) feet or more before branching. See FIG. 1C.

Trunk: Heavily fissured bark with light yellowish gray (RHS 156B) raised areas and darker orangish yellow (RHS 165D) recessed areas. See FIG. 2B. Size increases approximately one-half (0.5 cm) centimeters per growing season.

Branches: Current year shoots are the same, yellow-green color as the leaves. Red variations remain only on the sunny side and change to leaf vein color, then changing to a light yellowish gray (RHS 156B). Shoots are orangish yellow (RHS 165D), atypical for *Acer truncatum*. Late season current shoots can display a darker, orange-brown (RHS 166C) — pale yellow (RHS 19C) color in winter, similar to the leaf but darker. Third year wood is very hard and dense. Lenticels are sparse, straw-colored and oval. See FIGS. 2B-2C.

Leaves:

*Size.*—Typically smaller than *Acer truncatum* varieties; six and one-half (6.5 cm) centimeters wide by six and eight-tenths (6.8 cm) centimeters long. Largest sampled: 8.7×9.7 centimeters. Smallest sampled: 5.0×5.6 centimeters.

*Shape.*—Truncate base typical of *Acer truncatum*. Glabrous with five (5) oblong-ovate lobes, deeply cut two-thirds of way from tip to leaf base. Margins entire and very wavy, except for late season summer growth, which has nearly flat margins due to Texas heat. Broad, triangular teeth on central lobes, sometimes occurring also on one or both neighboring lobes. Central lobes are unusually long and tapered, sometimes almost thread-like for a substantial portion of the tip when unfurling, widening as they mature. Acuminate apices and tufted, veined axils on the underside.

Figure 3A:
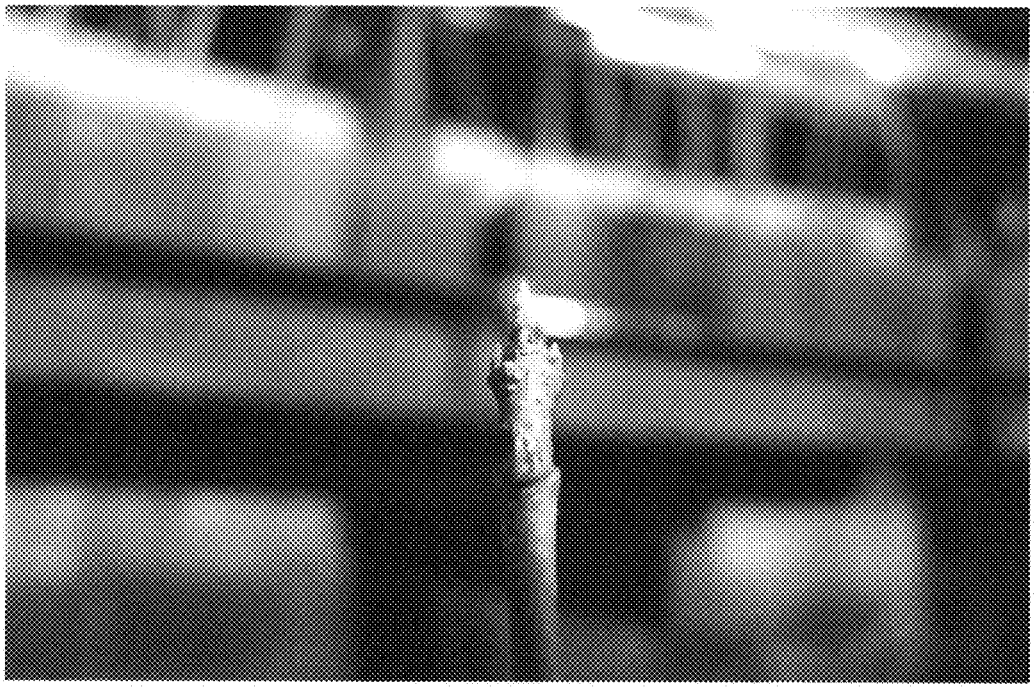
FIG. 3A is a photographic close-up of a typical terminal bud from the mature original tree of FIG. 1A.
Figure 3B:
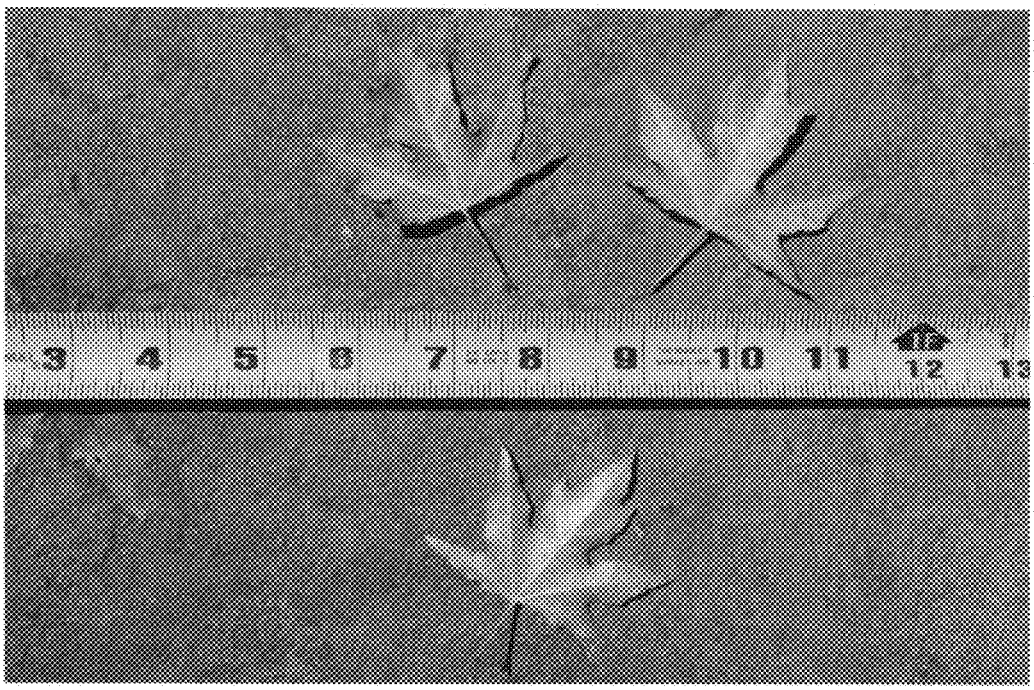
FIGS. 3B-3C are a photographic close-up views of individual leaves with varying coloration: summer old growth (FIG. 3B) and fall (FIG. 3C), typical of the mature original tree of FIG. 1A.
Figure 3C:
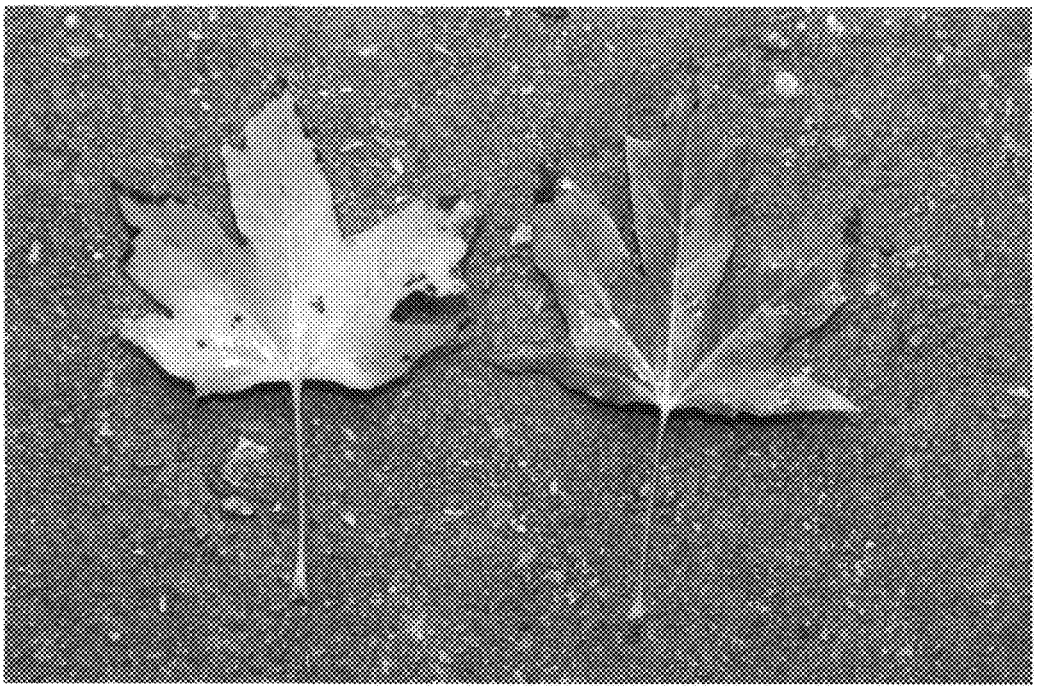
Figure 4A:
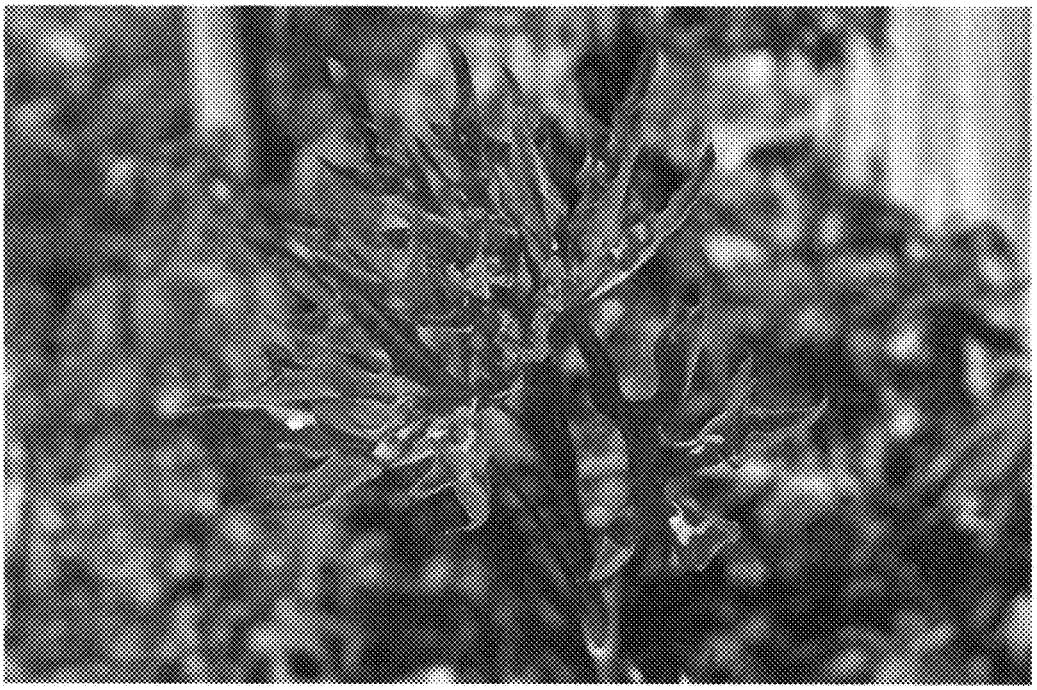
FIG. 4A is a photographic close-up view of early spring growth of the mature original tree of FIG. 1A.
Figure 4B:
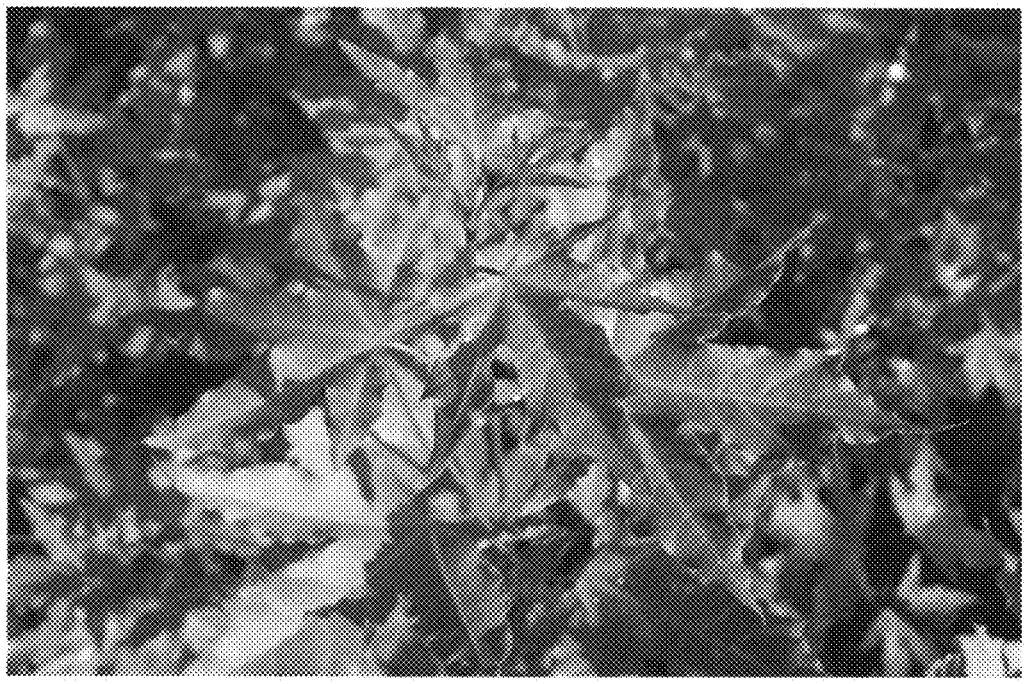
FIGS. 4B-4D are photographic close-up views of new-growth leaves exhibiting typical June color variations: red (FIG. 4B), pink (FIG. 4C) and orange (FIG. 4D) of the mature original tree of FIG. 1A.
Figure 4C:
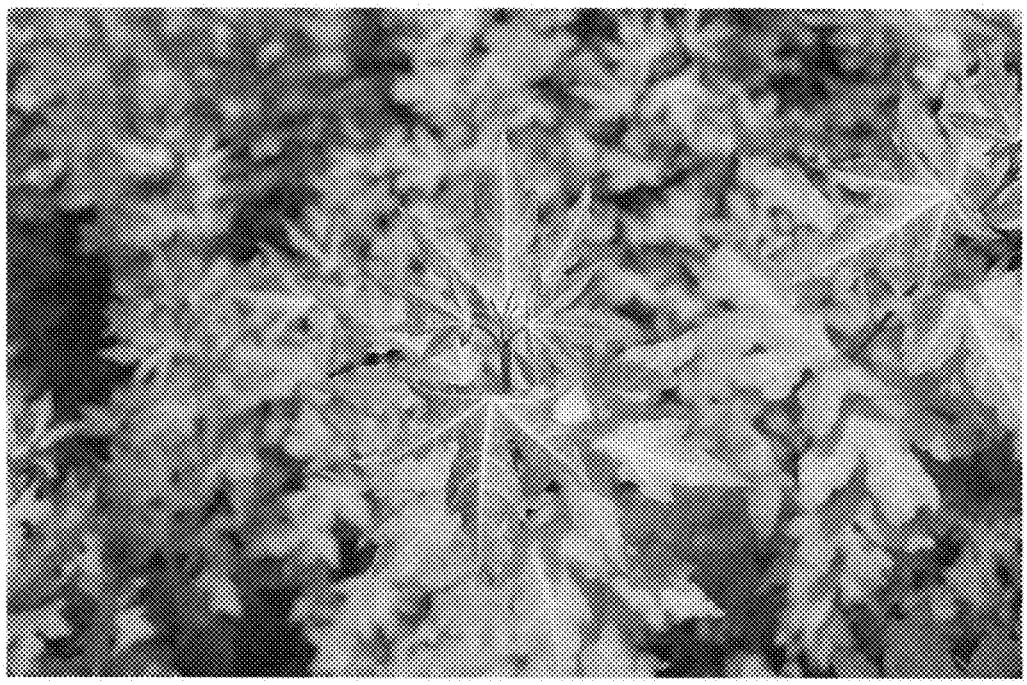
Figure 4D:
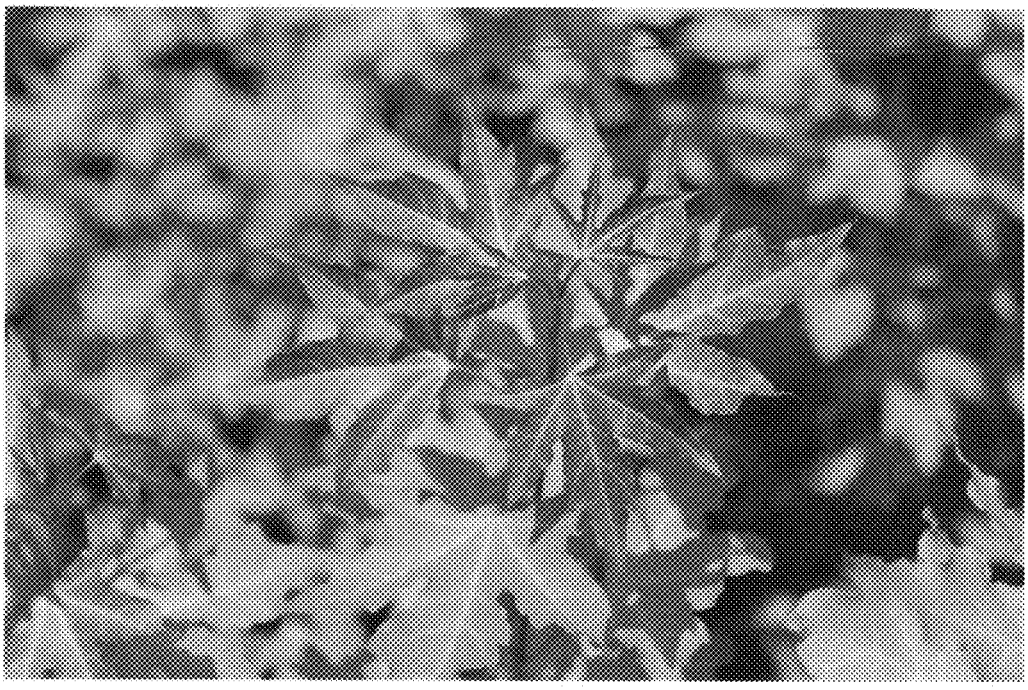
Figure 4E:
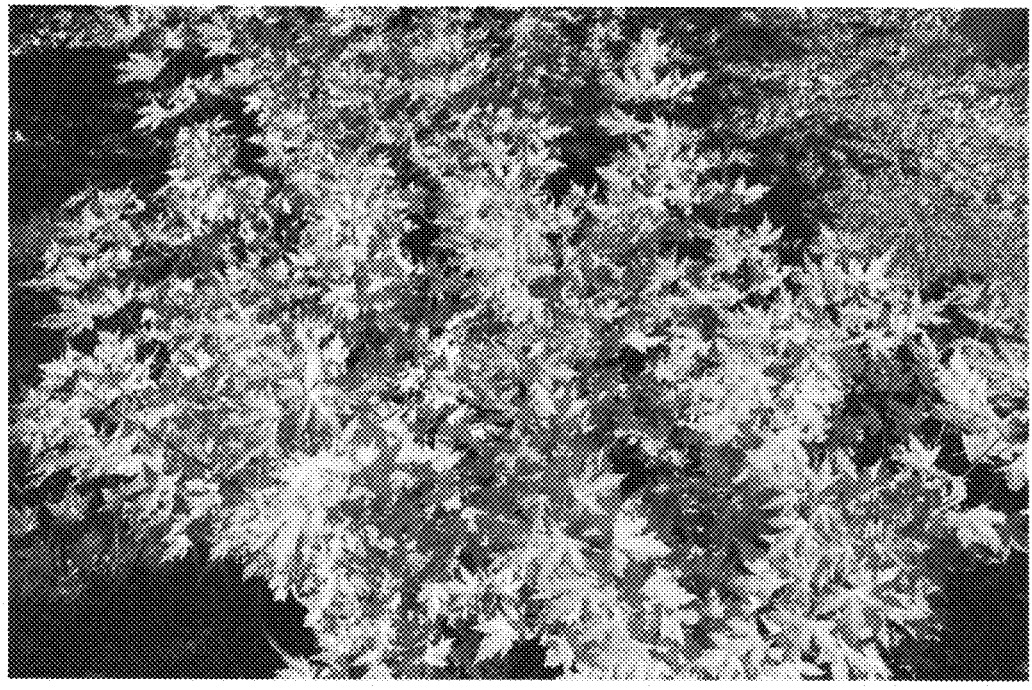
FIG. 4E is a photographic view of summer foliage on hardened branches, exhibiting summer coloration of new growth, of the mature original tree of FIG. 1A.
Figure 5A:
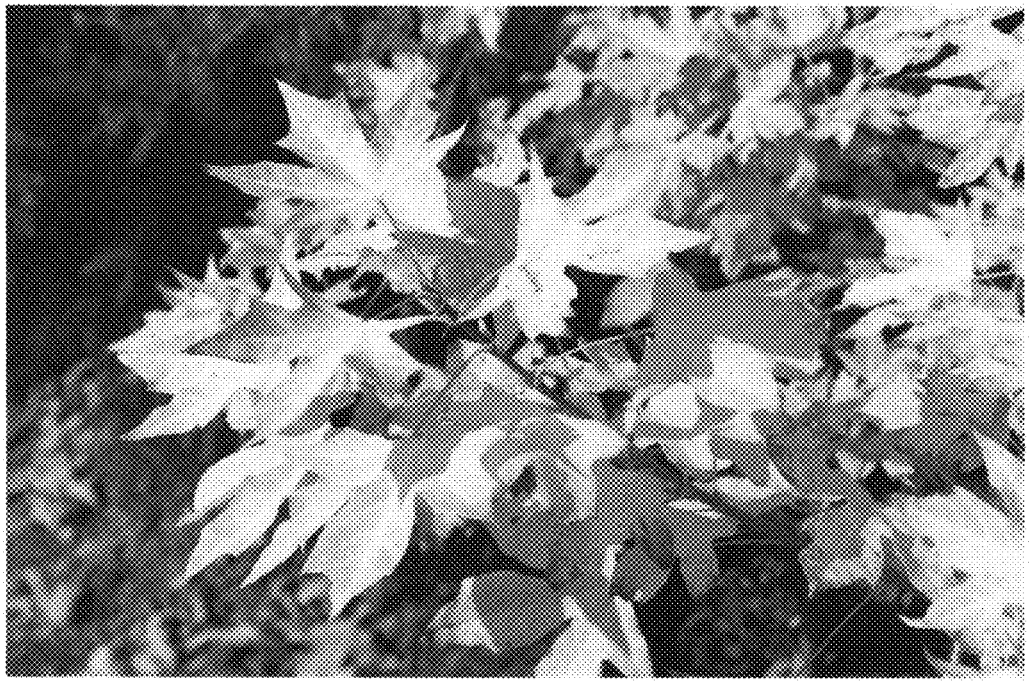
FIGS. 5A-5D are distant and close-up photographic views of fall leaves exhibiting yellow-green and red coloration variations.
Figure 5B:
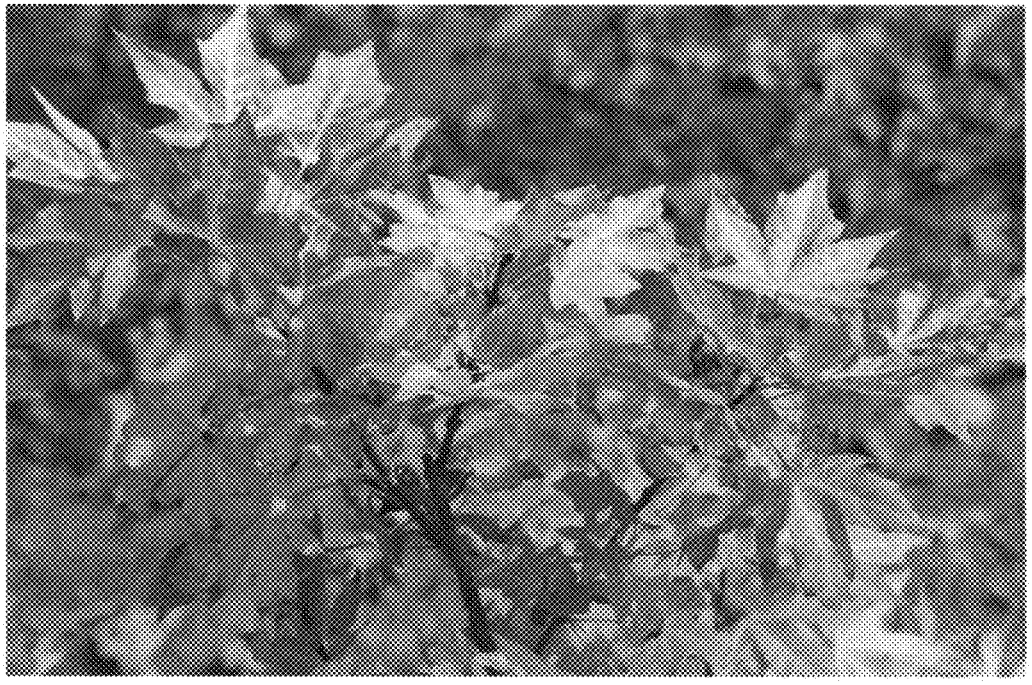
Figure 5C:
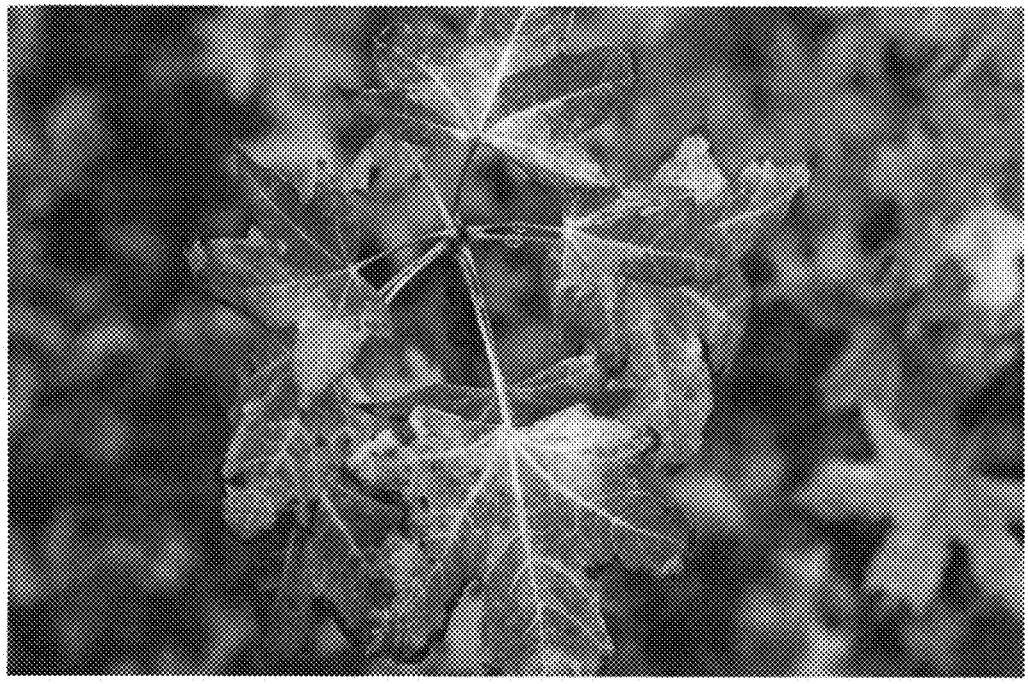
Figure 5D:
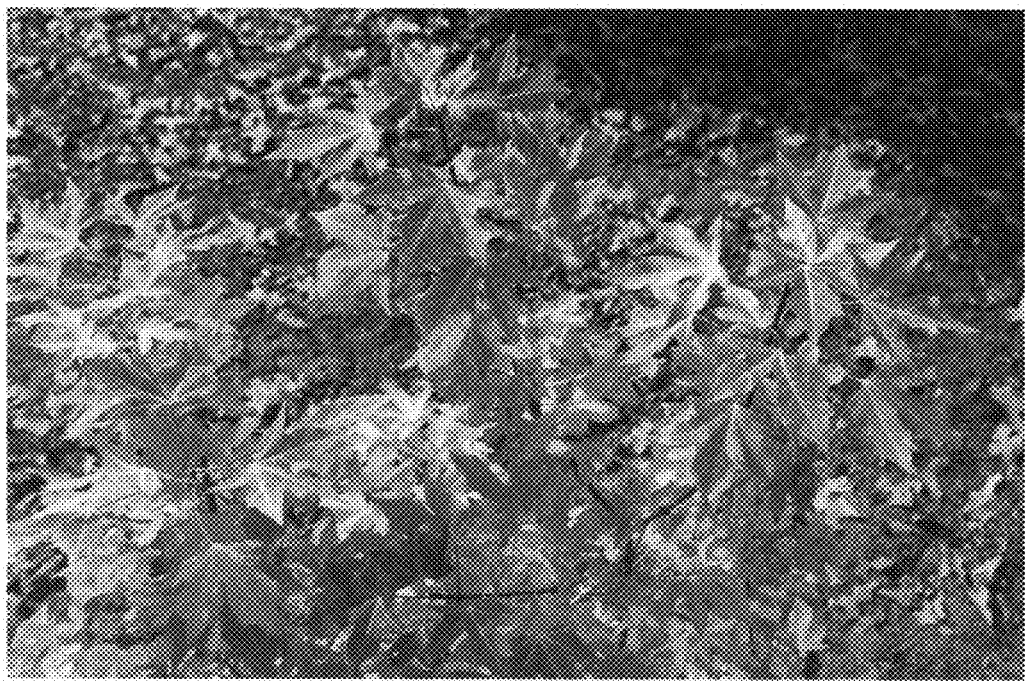
Figure 5E:
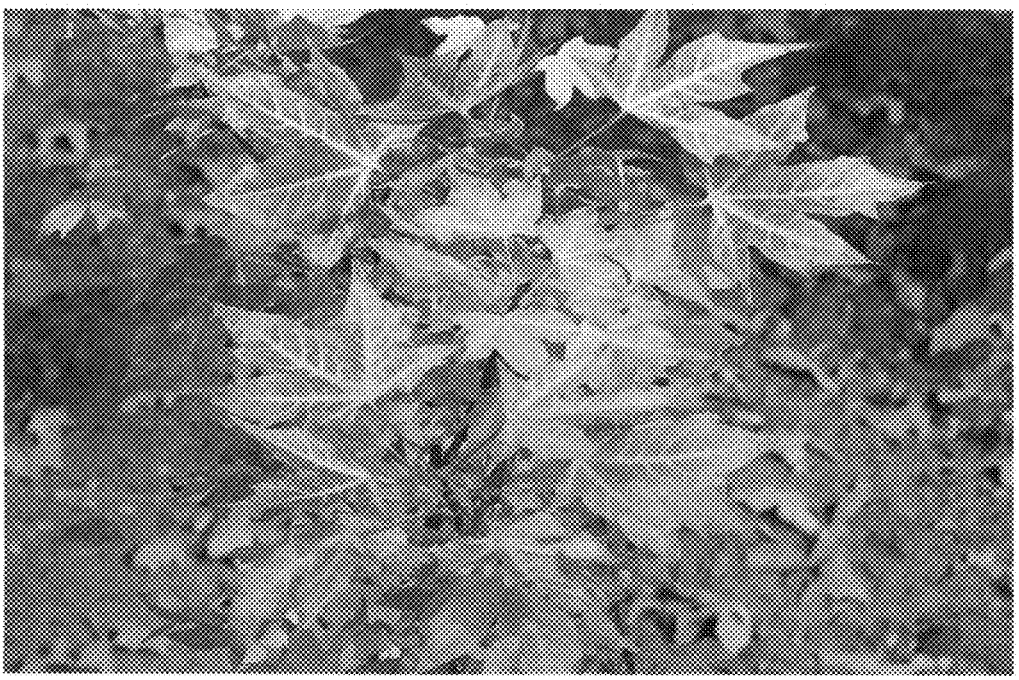
FIGS. 5E-5F are distant and close-up photographic views of fall leaves exhibiting the striking contrast between leave and vein coloration, and the almost white veins unique to this variety.
Figure 5F:
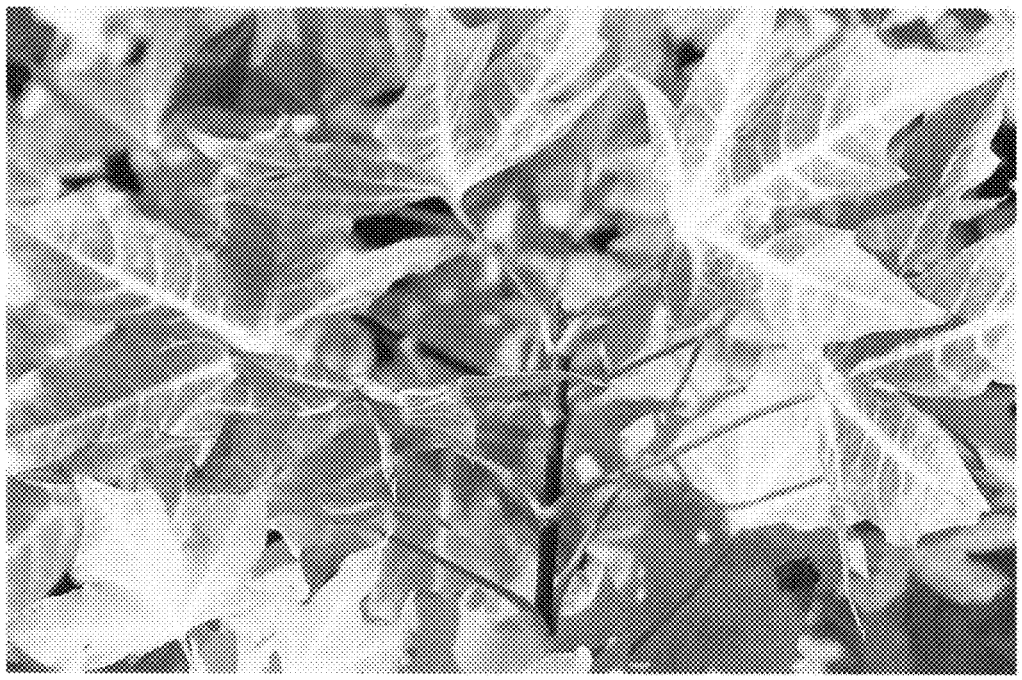
Figure 6:
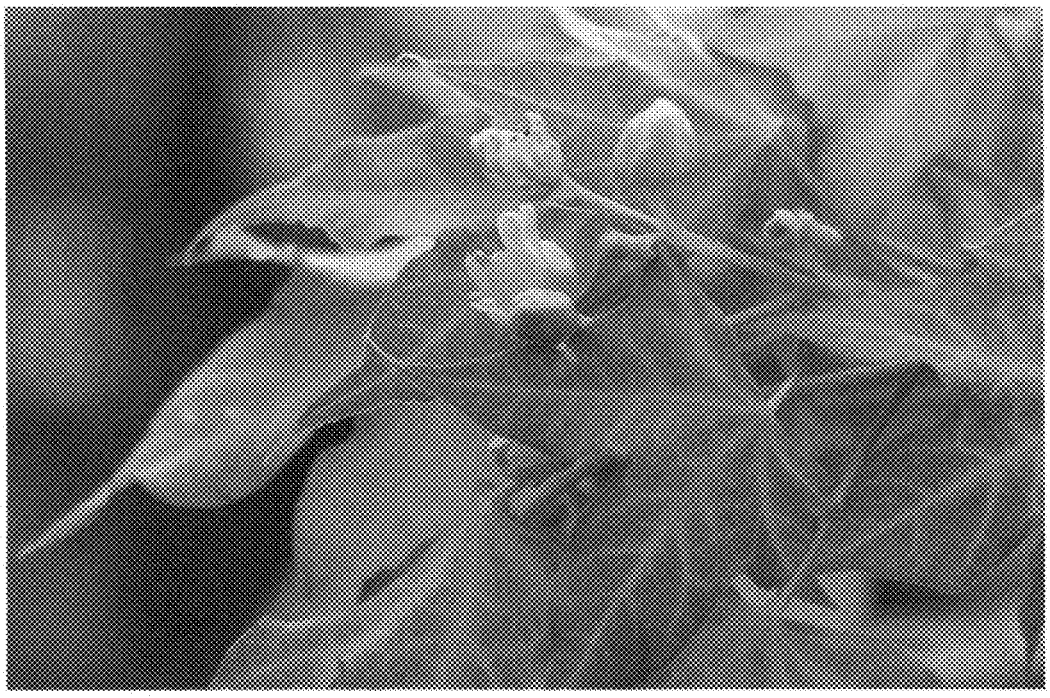
FIG. 6 is a photographic close-up view of flowers produced recently by the mature original tree of the present invention.

*Color.*—Waxy cuticle typical of *Acer truncatum,* creating a glossy shine at certain angles of sunlight. Leaves are the same color on top and bottom, with slightly, noticeably lighter colored, striking slightly raised veins on the both sides. See FIGS. 3B-3C. Brilliant yellowish green with brilliant, lighter yellowish-green veins, slightly greener in low light, shady conditions. All leaves on a single tree are uniform in color regardless of sunlight exposure (i.e. whether full sun or some shade). Early flush has moderate red-orange (RHS 35A) leaves with light orange-yellow (RHS 22C) veins giving them a distinctive coloration. Full early spring leaf coloration develops the same light orange-yellow (RHS 22C) of the early veins, while the veins turn a bright yellow green (RHS 150C). Later spring leaves develop a yellow-green (RHS 150C) coloration, darkening to a darker yellow (RHS 154C) in late June to July. Late spring and summer veins, however, retain their bright yellow-green (RHS 150D) coloration, appearing white (atypical of other Shantung maples) and creating a stunning contrast with the summer leaf colors. Summer new growth during hot weather prevalent in Texas can be red (RHS 35C) (FIG. 4D), pink (RHS 35D) (FIG. 4C) and orange (RHS 28C) (FIG. 4B). Hardened growth foliage has the same coloration on both the tops and bottoms of the leaves. See FIGS. 1A-1C, 3B. Fall coloration exhibits red (RHS 35C) (FIG. 5C), pink (RHS 35D) (FIG. 5D) and orange (RHS 28C) (FIGS. 5E-5F) color variations.

Petiole: Slender, same color as new growth, slowly changing to the colors of the leaf veins. Six (6 cm.) in length, glabrous. See FIGS. 3B-3C, 5C. Milky sap produced when broken.

Winter buds: Terminal buds three millimeters long by one and one-half millimeters wide (3×1.5 mm), usually brown grey. Occasionally terminal buds on soft shoots (late season growth) display a dark red and yellow tone all winter. Lateral buds generally similar but smaller (2 mm×1 mm). See FIG. 3A.

Flowering: The same as *Acer truncatum*. Flowering season is Spring (mid-March in Texas), before or simultaneously with leaves on terminal, typically forty by forty to sixty (40×40-60 mm) millimeter corymbose racemes having unequal, ten to twenty (10-20 mm.) millimeter length stems. Each 5-merous bloom is deep saucer-shaped, ten (10 mm) millimeters long and eight (8 mm) deep, with oblong to ovate petals and supported on one (1 cm) centimeter pedicels. Straw yellow (RHS 3C) color.

Reproductive organs: The same as *Acer truncatum*, being imperfect; monoecious; trees first produce blooms of one gender, then of the other, then of the first again, often having both at the same time; approximately half of trees begin with each gender. *Acer truncatum* blooms have a central, circular, slightly lobed, straw yellow (RHS 3C) pistil with an ovary supported on two divergent stigma arms with short, one (1 mm) styles. Pistil is surrounded by eight to ten (8-10) one (1 mm) millimeter, glabrous stamens with numerous oval, two (2 mm) millimeter anthers on five to six (5-6 mm) millimeter filaments. In male flowers, filaments are longer, sometimes extending the anthers above the perianth, with a diminished pistil and vestigial ovary. Female blooms have shorter filaments wherein the smaller anthers are almost concealed within the perianth.

Pollen: The same as *Acer truncatum*, having same color as flowers (straw yellow — RHS 3C).

Fruit: None observed to date.

Disease resistance: No known problems.

Climate: Adapts well to any well-drained soil, even highly alkaline, clay soils. Very drought, wind and direct sunlight tolerant. Extremely hardy to at least Zone 5 and possibly to Zone 4 (USDA hardness guidelines). As drought and sunshine tolerant as *Acer truncatum*, it exhibits a good ability to keep healthy new growth without wilting under extreme heat and direct, intense sunlight conditions, as well as thriving in shady environments.

In comparison to *Acer truncatum*, 'Super Dragon' maples demonstrate:

*Crown.*—Similar rounded crown; smaller expected height and spread.

*Trunk.*—Similar heavily fissured trunk, with light yellowish gray raised areas between darker orangish yellow fissures.

*Flowers.*—Similar straw-yellow, identical in size.

*Reproductive organs.*—Similar monoecious imperfect, pollen same color as blooms.

*Fruit.*—None observed to date.

*Leaf color.*—Brilliant yellowish-green colors, with lighter, yellowish-green veins consistently throughout the year and on both sides of the leaf. New growth exhibits red-orange (RHS 35A) with light orange-yellow (RHS 22C) veins, maturing in early Spring to orange-yellow (RHS 22C) leaves with bright yellow-green (RHS 150C) veins. By summer, leaves become a darker yellow (RHS 154C) but retaining bright (RHS 150D) veins. Typical *Acer truncatum* leaves, by contrast, turn a spinach-green (RHS 140A) on the top with a slightly lighter (RHS 140c) color on the bottom after Spring. Fall coloration of Super Dragon exhibits a distinctive red (RHS 35C) pink (RHS 35D) and orange (RHS 28C) tones with strikingly contrasting, almost white veins, in comparison to the normal yellow to orange with occasional red areas of typical *Acer truncatum.*

*Leaf shape and size.*—Glabrous, with truncated leaf bases typical of Shantung maples. 'Super Dragon' always has five, oblong-ovate lobes, and is deeply cut between lobes approximately two-thirds of distance between tip and leaf base. Margins are entire and wavy, similar to most of Shantung population but wavier than most. Central lobes have large, broad triangular teeth which sometimes occur on adjacent side lobes. Typical central lobe appears longer than normal, almost thread-like when unfurling, widening as it matures. Leaf size averages 6.5 centimeters, 2.5 centimeters smaller than typical of Shantung maples.

*Hardiness.*—As heat and drought tolerant. Where most *Acer truncatum* cultivars survive reliably in the extreme climate conditions, alkaline soils and urban pollution conditions of North Texas, 'Super Dragon' maples seem to have a rare ability to withstand full sunshine and heat in which other yellow-leaf maples easily burn. 'Super Dragon' maples can withstand full sun in the Midwest and lower South, and is extremely hardy to at least Zone 5 and possibly Zone 4. It thrives in said conditions, keeping healthy new growth without wilting even in extreme heat conditions, yet is tolerant of ice and wind storms, and is equally comfortable in low light or bright sunny locations.

I claim:

1. A new and distinct variety of an *Acer truncatum* maple tree named 'Super Dragon', as described and illustrated herein.

* * * * *